United States Patent
Tyrrell et al.

(10) Patent No.: US 11,076,907 B2
(45) Date of Patent: Aug. 3, 2021

(54) TISSUE SEALING FORCEPS

(71) Applicant: COVIDIEN LP, Mansfield, MA (US)

(72) Inventors: Barbara R. Tyrrell, Erie, CO (US); Duane E. Kerr, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 930 days.

(21) Appl. No.: 15/464,447

(22) Filed: Mar. 21, 2017

(65) Prior Publication Data
US 2017/0189100 A1    Jul. 6, 2017

Related U.S. Application Data

(63) Continuation of application No. 13/162,814, filed on Jun. 17, 2011, now Pat. No. 9,615,877.

(51) Int. Cl.
*A61B 18/12*    (2006.01)
*A61B 18/14*    (2006.01)
(Continued)

(52) U.S. Cl.
CPC ........ *A61B 18/1445* (2013.01); *A61B 17/285* (2013.01); *A61B 2017/320028* (2013.01);
(Continued)

(58) Field of Classification Search
CPC .............. A61B 18/1445; A61B 17/285; A61B 2018/146; A61B 2018/00482;
(Continued)

(56) References Cited

U.S. PATENT DOCUMENTS

| 3,651,233 A | 3/1972 | Rubricius |
| D249,549 S | 9/1978 | Pike |
(Continued)

FOREIGN PATENT DOCUMENTS

| CN | 201299462 | 9/2009 |
| DE | 2415263 A1 | 10/1975 |
(Continued)

OTHER PUBLICATIONS

Int'l Search Report EP 07 021647.8 dated May 2, 2008.
(Continued)

*Primary Examiner* — Ronald Hupczey, Jr.
*Assistant Examiner* — Yasamin Ekrami
(74) *Attorney, Agent, or Firm* — Carter, DeLuca & Farrell LLP

(57) ABSTRACT

A forceps includes an end effector assembly having first and second jaw members. One (or both) of the jaw members is moveable relative to the other between a spaced-apart position and an approximated position for grasping tissue therebetween. One (or both) of the jaw members includes an opposed jaw surface having an electrically-conductive tissue sealing plate disposed thereon. The electrically-conductive tissue sealing plate includes a first portion configured to conduct energy through tissue grasped between the jaw members to create a main tissue seal and a second portion including a plurality of spaced-apart fingers extending from the first portion. The second portion is configured to conduct energy through tissue grasped between the jaw members to create an auxiliary tissue seal extending from the main tissue seal for reducing stress concentrations adjacent the main tissue seal.

14 Claims, 6 Drawing Sheets

(51) Int. Cl.
*A61B 17/285* (2006.01)
*A61B 18/00* (2006.01)
*A61B 17/32* (2006.01)

(52) U.S. Cl.
CPC .............. *A61B 2018/0063* (2013.01); *A61B 2018/00196* (2013.01); *A61B 2018/00482* (2013.01); *A61B 2018/00958* (2013.01); *A61B 2018/146* (2013.01)

(58) Field of Classification Search
CPC ......... A61B 2018/00196; A61B 2017/320028; A61B 2018/00958; A61B 2018/0063
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,443,463 A | 8/1995 | Stern et al. |
| D384,413 S | 9/1997 | Zlock et al. |
| 5,665,100 A | 9/1997 | Yoon |
| H001745 H | 8/1998 | Paraschac |
| 5,833,695 A | 11/1998 | Yoon |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H001904 H | 10/2000 | Yates et al. |
| 6,152,923 A | 11/2000 | Ryan |
| D449,886 S | 10/2001 | Tetzlaff et al. |
| 6,334,860 B1 | 1/2002 | Dorn |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H002037 H | 7/2002 | Yates et al. |
| 6,451,018 B1 | 9/2002 | Lands et al. |
| D465,281 S | 11/2002 | Lang |
| D466,209 S | 11/2002 | Bon |
| 6,527,771 B1 | 3/2003 | Weadock et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,887,240 B1 | 5/2005 | Lands et al. |
| 6,905,497 B2 | 6/2005 | Truckai et al. |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| 7,160,299 B2 | 1/2007 | Baily |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| 7,381,209 B2 | 6/2008 | Truckai et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,776,036 B2 | 8/2010 | Schechter et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 8,147,489 B2 | 4/2012 | Moses et al. |
| 8,298,233 B2 | 10/2012 | Mueller |
| 8,394,096 B2 | 3/2013 | Moses et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,877 B2 | 4/2013 | Kerr et al. |
| 8,439,913 B2 | 5/2013 | Horner et al. |
| 8,469,716 B2 | 6/2013 | Fedotov et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,540,749 B2 | 9/2013 | Garrison et al. |
| 8,551,091 B2 | 10/2013 | Couture et al. |
| 8,556,929 B2 | 10/2013 | Harper et al. |
| 8,568,397 B2 | 10/2013 | Horner et al. |
| 8,568,408 B2 | 10/2013 | Townsend et al. |
| 8,585,736 B2 | 11/2013 | Horner et al. |
| 8,597,295 B2 | 12/2013 | Kerr |
| 8,623,018 B2 | 1/2014 | Horner et al. |
| 8,641,712 B2 | 2/2014 | Couture |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,685,009 B2 | 4/2014 | Chernov et al. |
| 8,685,021 B2 | 4/2014 | Chernov et al. |
| 8,702,749 B2 | 4/2014 | Twomey |
| 8,734,445 B2 | 5/2014 | Johnson et al. |
| 8,740,898 B2 | 6/2014 | Chojin et al. |
| 8,745,840 B2 | 6/2014 | Hempstead et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |
| 8,840,639 B2 | 9/2014 | Gerhardt, Jr. et al. |
| 8,852,185 B2 | 10/2014 | Twomey |
| 8,858,553 B2 | 10/2014 | Chojin |
| 8,888,771 B2 | 11/2014 | Twomey |
| 8,888,775 B2 | 11/2014 | Nau, Jr. et al. |
| 8,900,232 B2 | 12/2014 | Ourada |
| 8,906,018 B2 | 12/2014 | Rooks et al. |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,175 B2 | 2/2015 | Twomey |
| 8,961,504 B2 | 2/2015 | Hoarau et al. |
| 8,968,283 B2 | 3/2015 | Kharin |
| 8,968,305 B2 | 3/2015 | Dumbauld et al. |
| 8,968,316 B2 | 3/2015 | Roy et al. |
| 8,968,357 B2 | 3/2015 | Mueller |
| 8,968,359 B2 | 3/2015 | Kerr et al. |
| 9,005,200 B2 | 4/2015 | Roy et al. |
| 9,017,372 B2 | 4/2015 | Artale et al. |
| 9,028,484 B2 | 5/2015 | Craig |
| 9,028,495 B2 | 5/2015 | Mueller et al. |
| 9,039,704 B2 | 5/2015 | Joseph |
| 9,039,732 B2 | 5/2015 | Sims et al. |
| 9,113,933 B2 | 8/2015 | Chernova et al. |
| 9,113,934 B2 | 8/2015 | Chernov et al. |
| 9,161,807 B2 | 10/2015 | Garrison |
| 9,265,568 B2 | 2/2016 | Chernov et al. |
| 9,333,002 B2 | 5/2016 | Garrison |

(56) References Cited

U.S. PATENT DOCUMENTS

| | | | |
|---|---|---|---|
| 9,381,059 B2 | 7/2016 | Garrison | |
| 9,456,870 B2 | 10/2016 | Chernov et al. | |
| 9,498,278 B2 | 11/2016 | Couture et al. | |
| 9,585,709 B2 | 3/2017 | Krapohl | |
| 9,615,877 B2 | 4/2017 | Tyrrell et al. | |
| 9,655,672 B2 | 5/2017 | Artale et al. | |
| 2002/0165541 A1* | 11/2002 | Whitman | A61B 90/98 606/48 |
| 2002/0177846 A1 | 11/2002 | Mulier et al. | |
| 2005/0113828 A1 | 5/2005 | Shields et al. | |
| 2007/0049920 A1 | 3/2007 | McClurken et al. | |
| 2007/0118115 A1 | 5/2007 | Artale et al. | |
| 2007/0156139 A1 | 7/2007 | Schechter et al. | |
| 2008/0015566 A1 | 1/2008 | Livneh | |
| 2008/0039836 A1 | 2/2008 | Odom et al. | |
| 2008/0132893 A1 | 6/2008 | D'Amelio et al. | |
| 2009/0048589 A1* | 2/2009 | Takashino | A61B 17/07207 606/28 |
| 2009/0131933 A1 | 5/2009 | Ghabrial et al. | |
| 2009/0248021 A1 | 10/2009 | McKenna | |
| 2011/0071523 A1 | 3/2011 | Dickhans | |
| 2011/0270245 A1 | 11/2011 | Horner et al. | |
| 2011/0270251 A1 | 11/2011 | Horner et al. | |
| 2011/0276049 A1 | 11/2011 | Gerhardt | |
| 2011/0295313 A1 | 12/2011 | Kerr | |
| 2011/0306965 A1* | 12/2011 | Norvell | A61B 18/1445 606/41 |
| 2012/0059372 A1 | 3/2012 | Johnson | |
| 2012/0059409 A1 | 3/2012 | Reschke et al. | |
| 2012/0083783 A1* | 4/2012 | Davison | A61B 18/1445 606/45 |
| 2012/0123404 A1 | 5/2012 | Craig | |
| 2012/0172868 A1 | 7/2012 | Twomey et al. | |
| 2012/0239034 A1 | 9/2012 | Horner et al. | |
| 2012/0265241 A1 | 10/2012 | Hart et al. | |
| 2012/0296205 A1 | 11/2012 | Chernov et al. | |
| 2012/0296238 A1 | 11/2012 | Chernov et al. | |
| 2012/0330308 A1 | 12/2012 | Joseph | |
| 2013/0018364 A1 | 1/2013 | Chernov et al. | |
| 2013/0018411 A1 | 1/2013 | Collings et al. | |
| 2013/0022495 A1 | 1/2013 | Allen, IV et al. | |

FOREIGN PATENT DOCUMENTS

| | | |
|---|---|---|
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 8712328 U1 | 2/1988 |
| DE | 04303882 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 10045375 A1 | 4/2002 |
| DE | 102004026179 | 12/2005 |
| DE | 202007009165 | 10/2007 |
| DE | 202007009317 | 10/2007 |
| DE | 202007016233 | 3/2008 |
| DE | 102008018406 | 7/2009 |
| EP | 1159926 A3 | 3/2003 |
| EP | 2111812 A2 | 10/2009 |
| JP | 61501068 | 9/1984 |
| JP | 6502328 | 3/1992 |
| JP | 55106 | 1/1993 |
| JP | H05-40112 A | 2/1993 |
| JP | 6121797 | 5/1994 |
| JP | 6511401 | 12/1994 |
| JP | H06-343644 A | 12/1994 |
| JP | H07-265328 A | 10/1995 |
| JP | 856955 | 5/1996 |
| JP | H08-252263 A | 10/1996 |
| JP | 8317934 | 12/1996 |
| JP | 910223 | 1/1997 |
| JP | 9122138 | 5/1997 |
| JP | 1024051 | 1/1998 |
| JP | 10155798 | 6/1998 |
| JP | 1147150 | 2/1999 |
| JP | 11070124 | 3/1999 |
| JP | 11169381 | 6/1999 |
| JP | 11192238 | 7/1999 |
| JP | 11244298 A | 9/1999 |
| JP | 2000102545 A | 4/2000 |
| JP | 2000342599 A | 12/2000 |
| JP | 2000350732 A | 12/2000 |
| JP | 20018944 | 1/2001 |
| JP | 200129356 | 2/2001 |
| JP | 2001128990 A | 5/2001 |
| JP | 2001190564 A | 7/2001 |
| JP | 2004517668 A | 6/2004 |
| JP | 2004528869 A | 9/2004 |
| SU | 401367 A1 | 10/1973 |
| WO | 0036986 A1 | 6/2000 |
| WO | 0115614 A1 | 3/2001 |
| WO | 0154604 A1 | 8/2001 |
| WO | 05110264 A3 | 4/2006 |

OTHER PUBLICATIONS

Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.

(56) References Cited

OTHER PUBLICATIONS

Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 12171992.6 dated Sep. 5, 2012.
U.S. Appl. No. 08/926,869, filed Sep. 10, 1997; inventor: Chandler.
U.S. Appl. No. 09/177,950, filed Oct. 23, 1998; inventor: Frazier.
U.S. Appl. No. 09/387,883, filed Sep. 1, 1999; inventor:Schmaltz.
U.S. Appl. No. 09/591,328, filed Jun. 9, 2000; inventor: Ryan.
U.S. Appl. No. 12/336,970, filed Dec. 17, 2008; inventor: Sremcich.
Michael Choti, "Abdominoperineal Resection with the LigaSure Vessel Sealing System and LigaSure ; Atlas 20 cm Open Instrument"; Innovations That Work, Jun. 2003.
Chung et al., "Clinical Experience of Sutureless Closed Hemorrhoidectomy with LigaSure"; Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, Vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy"; Sales/Product Literature; Jan. 2004.
E. David Crawford "Evaluation of a New Vessel Sealing Device in Urologic Cancer Surgery"; Sales/Product Literature 2000.
Johnson et al. "Evaluation of the LigaSure Vessel Sealing System in Hemorrhoidectormy"; American College of Surgeons (ACS) Clinicla Congress Poster (2000).
Muller et al., "Extended Left Hemicolectomy Using the LigaSure Vessel Sealing System"; Innovations That Work, Sep. 1999.
Kennedy et al. "High-burst-strength, feedback-controlled bipolar vessel sealing"; Surgical Endoscopy (1998) 12:376-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery"; Innovations That Work, Jun. 2002.
Heniford et al. "Initial Research and Clinical Results with an Electrothermal Bipolar Vessel Sealer"; Oct. 1999.
Heniford et al. "Initial Results with an Electrothermal Bipolar Vessel Sealer"; Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents"; Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy"; Innovations That Work, Nov. 2002.
Sigel et al. "The Mechanism of Blood Vessel Closure by High Frequency Electrocoagulation"; Surgery Gynecology & Obstetrics, Oct. 1965 pp. 823-831.
Sampayan et al, "Multilayer Ultra-High Gradient Insulator Technology"; Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy"; The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females"; Current Surgical Techniques in Urology, vol. 14, Issue 3, 2001.
Palazzo et al. "Randomized clinical trial of Ligasure versus open haemorrhoidectomy"; British Journal of Surgery 2002, 89, 154-157.
Levy et al. "Randomized Trial of Suture Versus Electrosurgical Bipolar Vessel Sealing in Vaginal Hysterectomy" Dbstetrics & Gynecology, vol. 102, No. 1, Jul. 2003.
"Reducing Needlestick Injuries in the Operating Room"; Sales/Product Literature 2001.
Bergdahl et al. "Studies on Coagulation and the Development of an Automatic Computerized Bipolar Coagulator" J. Nieurosurg, vol. 75, Jul. 1991, pp. 148-151.
Strasberg et al. "A Phase I Study of the LigaSure Vessel Sealing System in Hepatic Surgery"; Section of HPB Surger, Washington University School of Medicine, St. Louis MO, Presented at AHPBA, Feb. 2001.
Sayfan et al. "Sutureless Closed Hemorrhoidectomy: A New Technique"; Annals of Surgery vol. 234 No. 1 Jul. 2001; pp. 21-24.
Levy et al., "Update on Hysterectomy—New Technologies and Techniques"; OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy"; FIGO 2000, Washington, D.C.

(56) References Cited

OTHER PUBLICATIONS

E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue"; MICCAI 2005; LNCS 3750 pp. 624-632, dated: 2005.
McLellan et al. "Vessel Sealing for Hemostasis During Pelvic Surgery"; Int'l Federation of Gynecology and Obstetrics FIGO World Congress 2000, Washington, D.C.
McLellan et al. "Vessel Sealing for Hemostasis During Gynecologic Surgery"; Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 040277055 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.

* cited by examiner

TISSUE SEALING FORCEPS

CROSS-REFERENCE TO RELATED APPLICATIONS

This application is a continuation application of U.S. application Ser. No. 13/162,814, filed Jun. 17, 201, the entire contents of which are hereby incorporated herein by reference.

BACKGROUND

Technical Field

The present disclosure relates to surgical instruments and, more particularly, to a surgical instrument for luminal tissue sealing, e.g., bowel sealing.

Background of Related Art

Electrosurgical instruments, e.g., electrosurgical forceps, utilize both mechanical clamping action and electrical energy to affect hemostasis by heating tissue to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue.

As can be appreciated, in order to create an effective tissue seal, different considerations are taken into account depending on the characteristics, e.g., composition, structure and/or function, of the tissue to be sealed. For example, in order to effectively seal the bowel, it is important to consider the stresses imparted on the seal as a result of distention of the bowel as well as peristaltic reactions within the bowel.

SUMMARY

In accordance with one embodiment of the present disclosure, a forceps is provided. The forceps includes an end effector assembly having first and second jaw members. One (or both) of the jaw members is moveable relative to the other between a spaced-apart position and an approximated position for grasping tissue therebetween. One (or both) of the jaw members includes an opposed jaw surface having an electrically-conductive tissue sealing plate disposed thereon. The electrically-conductive tissue sealing plate includes a first portion configured to conduct energy through tissue grasped between the jaw members to create a main tissue seal and a second portion including a plurality of spaced-apart fingers extending from the first portion. The second portion is configured to conduct energy through tissue grasped between the jaw members to create an auxiliary tissue seal extending from the main tissue seal for reducing stress concentrations adjacent the main tissue seal.

In one embodiment, the first portion of the electrically-conductive tissue sealing plate defines a generally arcuate configuration.

In yet another embodiment, the electrically-conductive tissue sealing plate is disposed at a distal end of jaw member.

In still another embodiment, the opposed jaw surface includes an electrically-conductive main seal portion, an electrically-conductive auxiliary seal portion, and an electrically-insulative tissue grasping portion.

In still yet another embodiment, the forceps includes first and second switches. The first and second switches are selectively and independently activatable for controlling the supply of energy to the first and second portions, respectively, of the electrically-conductive tissue sealing plate.

In accordance with another embodiment of the present disclosure, a forceps is provided. The forceps includes an end effector assembly having first and second jaw members. One (or both) of the jaw members is moveable relative to the other between a spaced-apart position and an approximated position for grasping tissue therebetween. One (or both) of the jaw members includes an opposed jaw surface. The opposed jaw surface includes an electrically-conductive tissue sealing plate disposed thereon. The electrically-conductive tissue sealing plate is configured to conduct energy through tissue grasped between the jaw members to create a tissue seal. The opposed jaw surface further includes a plurality of thermal damage elements disposed thereon. The thermal damage elements are configured to conduct energy through tissue to thermally-damage tissue adjacent the tissue seal.

In one embodiment, the electrically-conductive tissue sealing plate defines a generally arcuate configuration.

In another embodiment, the electrically-conductive tissue sealing plate and the thermal damage elements are disposed toward a distal end of the jaw member.

In yet another embodiment, the thermal damage elements are spaced-apart relative to one another.

In still another embodiment, the opposed jaw surface includes an electrically-conductive tissue sealing portion, an electrically-conductive thermal damage portion, and an electrically-insulative tissue grasping portion.

In still yet another embodiment, the forceps includes first and second switches. The first and second switches are selectively and independently activatable for controlling the supply of energy to the electrically-conductive tissue sealing plate and the thermal damage elements, respectively.

In accordance with yet another embodiment of the present disclosure, a forceps is provided. The forceps includes an end effector assembly having first and second jaw members. One (or both) of the jaw members is moveable relative to the other between a spaced-apart position and an approximated position for grasping tissue therebetween. One (or both) of the jaw members includes an opposed jaw surface having an electrically-conductive tissue sealing plate disposed thereon. The electrically-conductive tissue sealing plate includes a first portion configured to conduct energy through tissue grasped between the jaw members to create a main tissue seal and a second portion configured to conduct energy through tissue grasped between the jaw members to create an auxiliary tissue seal extending from the main tissue seal for reducing stress concentrations adjacent the main tissue seal. First and second switches are operably coupled to the first and second portions, respectively, and are selectively and independently activatable for controlling the supply of energy to the first and second portions, respectively. The forceps may further be configured similarly to any of the above embodiments.

Another embodiment of a forceps provided in accordance with the present disclosure includes an end effector assembly having first and second jaw members. One (or both) of the jaw members is moveable relative to the other between a spaced-apart position and an approximated position for grasping tissue therebetween. One (or both) of the jaw members includes an opposed jaw surface including an electrically-conductive main seal portion, an electrically-conductive auxiliary seal portion, and an electrically-insulating tissue grasping portion. The main seal portion is configured to conduct energy through tissue grasped between the jaw members to create a main tissue seal. The auxiliary seal portion includes a plurality of spaced-apart components and is configured to conduct energy through tissue grasped between the jaw members to create an auxiliary tissue seal for reducing stress concentrations adjacent the main tissue seal. The tissue grasping portion is configured to grasp tissue between the jaw members. A portion of the tissue grasping portion is disposed between the spaced-apart components of the auxiliary seal portion. The forceps may further be configured similarly to any of the above embodiments.

BRIEF DESCRIPTION OF THE DRAWINGS

Various embodiments of the present disclosure are described herein with reference to the drawings wherein.

DETAILED DESCRIPTION

Figure 1:
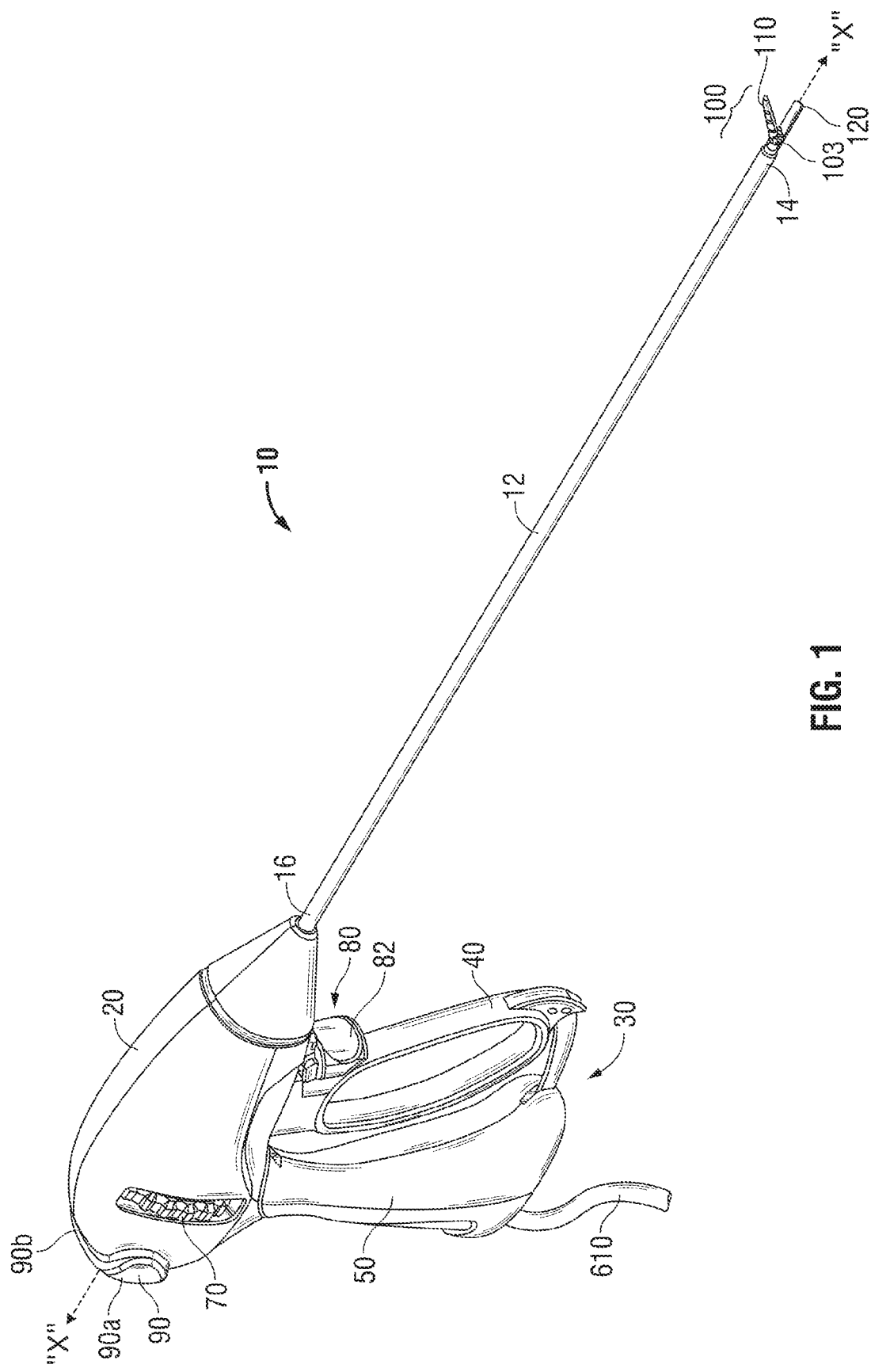
FIG. 1 is a front, perspective view of an endoscopic surgical instrument configured for use in accordance with the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
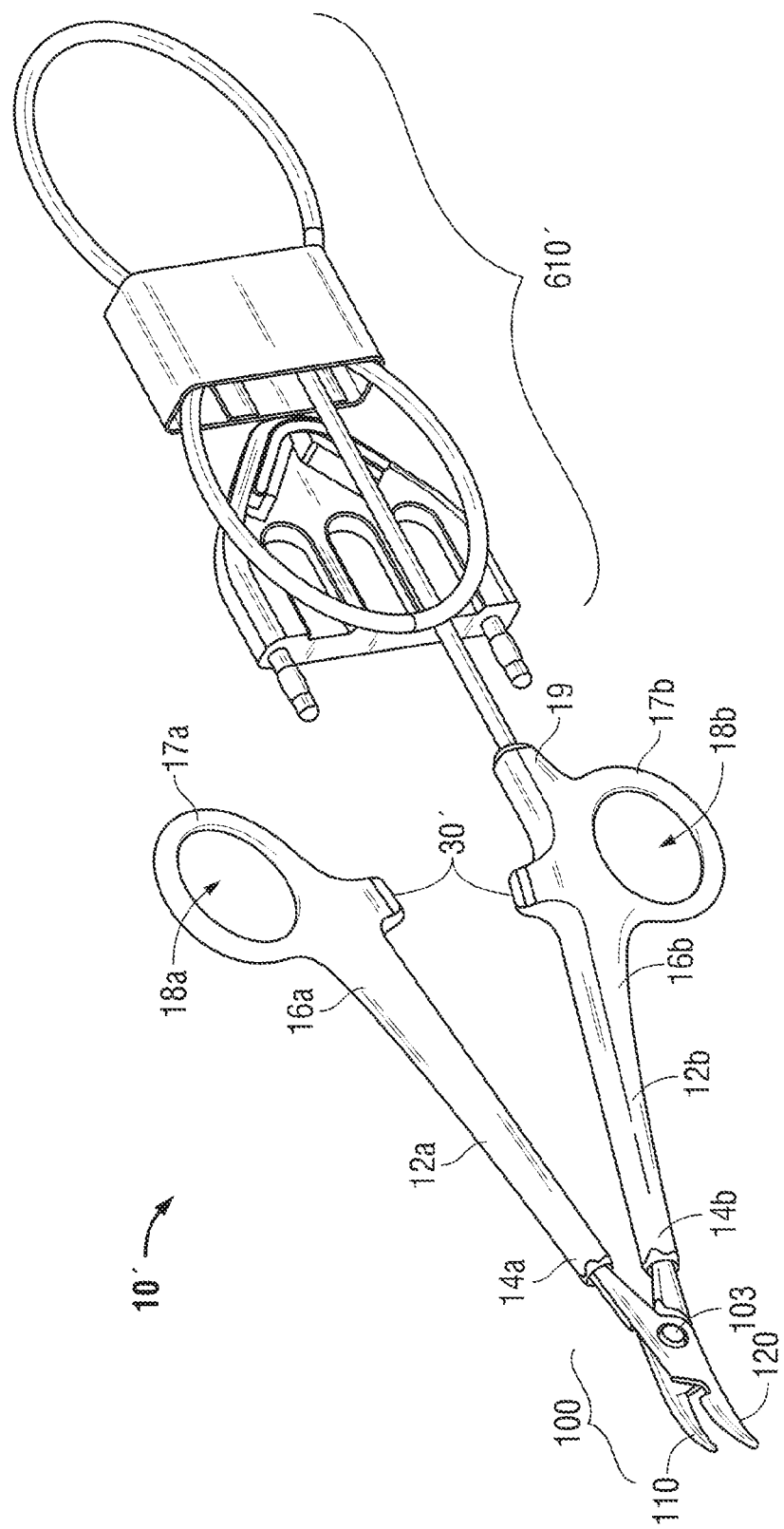
FIG. 2 is a front, perspective view of an open surgical instrument configured for use in accordance with the present disclosure.
Figure 3:
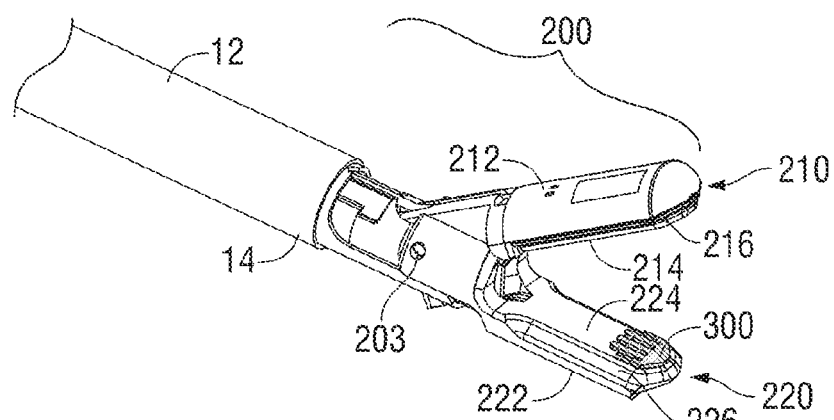
FIG. 3 is a front, perspective view of one embodiment of an end effector assembly configured for use with the surgical instrument of FIG. 1.

Referring now to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic instrument, e.g., forceps 10, or an open instrument, e.g., forceps 10', may be utilized in accordance with the present disclosure. Obviously, different electrical and mechanical connections and considerations apply to each particular type of instrument; however, the novel aspects with respect to the end effector assembly and its operating characteristics remain generally consistent with respect to both the open and endoscopic configurations.

Turning now to FIG. 1, an endoscopic forceps 10 is provided defining a longitudinal axis "X-X" and including a housing 20, a handle assembly 30, a rotating assembly 70, a trigger assembly 80, an actuator 90, and an end effector assembly 100. Forceps 10 further includes a shaft 12 having a distal end 14 configured to mechanically engage end effector assembly 100 and a proximal end 16 that mechanically engages housing 20. Housing 20 contains the internal working components of the forceps 10 which are not described herein but which may be found in commonly-owned U.S. Pat. No. 7,156,846.

End effector assembly 100 is shown attached at a distal end 14 of shaft 12 and includes a pair of opposing jaw members 110 and 120. Jaw members 110, 120 are moveable between a spaced-apart position and an approximated position for grasping tissue therebetween. End effector assembly 100 is designed as a unilateral assembly, e.g., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, e.g., where both jaw member 110 and jaw member 120 are moveable about a pivot 103 relative to one another and to shaft 12.

With continued reference to FIG. 1, forceps 10 also includes electrosurgical cable 610 that connects forceps 10 to a generator (not shown) or other suitable power source, although forceps 10 may alternatively be configured as a battery powered instrument. Cable 610 includes a wire (or wires) (not explicitly shown) extending therethrough that has sufficient length to extend through shaft 12 in order to provide electrical energy to at least one of the jaw members 110 and 120 of end effector assembly 100. Trigger 82 of trigger assembly 80 may be selectively depressed to advance a knife (not shown) between jaw members 110, 120 to cut tissue grasped therebetween. Actuator 90, on the other hand, is selectively activatable to supply electrosurgical energy to one (or both) of jaw members 110, 120, as will be described in greater detail below.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about a longitudinal axis "X-X" to rotate end effector 100 about longitudinal axis "X-X." Moveable handle 40 of handle assembly 30 is ultimately connected to a drive assembly (not shown) that, together, mechanically cooperate to impart movement of jaw members 110 and 120 between the spaced-apart position and the approximated position to grasp tissue disposed between jaw members 110, 120. As shown in FIG. 1, moveable handle 40 is initially spaced-apart from fixed handle 50 and, correspondingly, jaw members 110, 120 are in the spaced-apart position. Moveable handle 40 is depressible from this initial position to a depressed position corresponding to the approximated position of jaw members 110, 120.

Referring now to FIG. 2, an open forceps 10' is shown including two elongated shafts 12a and 12b, each having a proximal end 16a and 16b, and a distal end 14a and 14b, respectively. Similar to forceps 10 (FIG. 1), forceps 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that are pivotably connected about a pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another that, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet 30' may be included for selectively locking the jaw members 110 and 120 relative to one another at various positions during pivoting. Ratchet 30' may include graduations or other visual markings that enable the user to easily and quickly ascertain and control the amount of closure force desired between the jaw members 110 and 120.

With continued reference to FIG. 2, one of the shafts, e.g., shaft 12b, includes a proximal shaft connector 19 which is designed to connect the forceps 10' to a source of electrosurgical energy such as an electrosurgical generator (not shown). Proximal shaft connector 19 secures an electrosurgical cable 610' to forceps 10' such that the user may selectively apply electrosurgical energy to jaw member 110 and/or jaw member 120 of end effector assembly 100.

Referring now to FIGS. 3-5A, one embodiment of an end effector assembly provided in accordance with the present disclosure is shown generally identified by reference numeral 200. End effector assembly 200 may be adapted for use with either forceps 10 (FIG. 1), forceps 10' (FIG. 2), or any other suitable surgical instrument (not shown). However, as shown, end effector assembly 200 is disposed at distal end 14 of shaft 12 of forceps 10 (FIG. 1). Similar to end effector assembly 100, end effector assembly 200 includes first and second jaw members 210, 220, respectively, pivotably coupled to one another about pivot 203 and movable between a spaced-apart position and an approximated position for grasping tissue therebetween. As shown, end effector assembly 200 defines a unilateral configuration wherein jaw member 220 is fixed and jaw member 210 is movable relative to jaw member 220 between the spaced-apart and approximated positions. However, this configuration may be reversed, or end effector assembly 200 may be configured as a bilateral configuration, e.g., where both jaw members 210, 220 are moveable.

With continued reference to FIGS. 3-5A, each jaw member 210, 220 includes an outer jaw housing 212, 222 and an opposed, tissue-grasping surface 214, 224, respectively. Tissue-grasping surfaces 214, 224 of jaw members 210, 220, respectively, are formed at least partially from an electrically-insulative material. An electrically-conductive tissue sealing plate 300 is disposed at a respective distal end 216, 226 of each tissue-grasping surface 214, 224 such that tissue sealing plates 300 oppose one another. The tissue sealing plates 300 of jaw members 210, 220 are substantially similar and, thus, the tissue sealing plate of jaw member 210 is not shown or described herein to avoid unnecessary repetition.

Figure 5A:
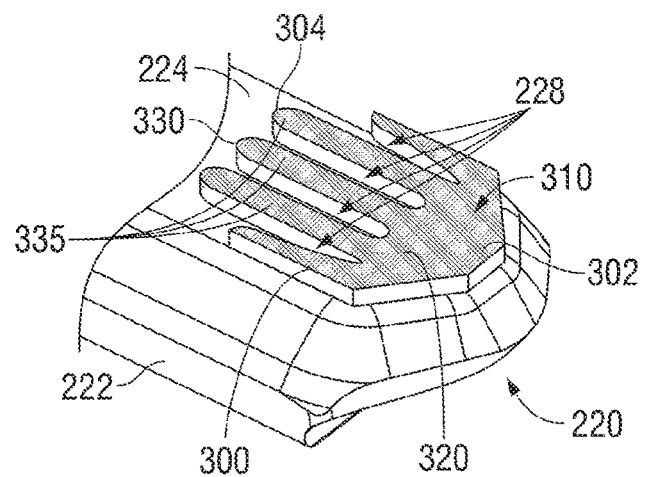
FIG. 5A is a greatly enlarged, side, perspective view of a distal end of the jaw member of FIG. 4.

As best shown in FIG. 5A, tissue sealing plate 300 defines a tissue sealing surface 310 that is raised relative to tissue-grasping surface 224, although tissue sealing surface 310 may alternatively be co-planar with tissue-grasping surface 224. In either configuration, as can be appreciated, when tissue is grasped between jaw members 210, 220, e.g., when jaw members 210, 220 are moved to the approximated position, at least a portion of tissue is disposed between tissue sealing plate 300 of jaw member 220 and the tissue sealing plate (not explicitly shown) of jaw member 210. As such, and as will be described in greater detail below, electrical energy may be conducted between the tissue sealing plates 300 of jaw members 210, 220 and through tissue to seal tissue grasped therebetween. Tissue sealing plate 300 may be adapted to connect to a source of electrosurgical energy in any suitable fashion. For example, tissue sealing plate 300 of jaw member 220 may include an electrically-conductive flange (not shown), or other suitable feature, that extends into jaw housing 222 of jaw member 220 such that tissue sealing plate 300 may be coupled to a source of electrosurgical energy via the wires of electrosurgical cable 610 (FIG. 1) that extend through shaft 12 and into jaw member 210 and/or jaw member 220 of end effector assembly 200.

Figure 4:
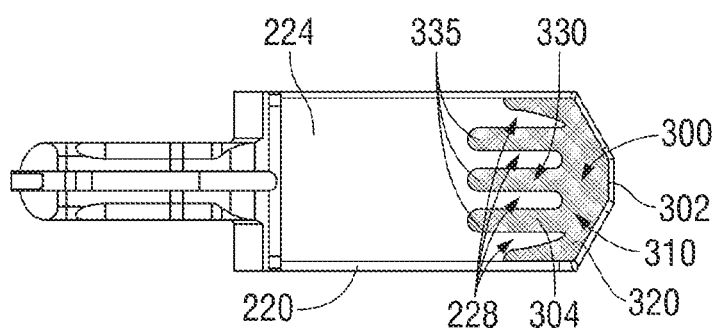
FIG. 4 is top view of one of the jaw members of the end effector assembly of FIG. 3.

With continued reference to FIGS. 3-5A, and as best shown in FIGS. 4-5A, tissue sealing plate 300 includes a main seal portion 320 at a distal end 302 thereof and an auxiliary seal portion 330 at a proximal end 304 thereof, although other suitable configurations may also be provided. As shown, main seal portion 320 and auxiliary seal portion 330 are integrally formed, although tissue sealing plate 300 may alternatively include separate main and auxiliary seal plate sections (not shown). Main seal portion 320 defines a generally arcuate configuration, while auxiliary seal portion 330 includes a plurality of fingers 335, e.g., three (3) fingers 335, although greater or fewer than three fingers 335 may be provided, that extend proximally from main seal portion 320. Fingers 335 of auxiliary seal portion 330 are spaced-apart from one another such that a portion 228 of tissue-grasping surface 224 is exposed between each of fingers 335 and between the outer fingers 335 and main seal portion 320. Further, as best shown in FIG. 4, fingers 335 extend proximally beyond the ends of arcuate-shaped main seal portion 320. However, other configurations of auxiliary seal portion 330 may also be provided, e.g., auxiliary seal portion 330 of tissue sealing plate 300 may include a plurality of spaced-apart elements similar to thermal damage elements 520 of jaw member 420 of end effector assembly 400 (see FIGS. 7-9A).

Figure 5B:
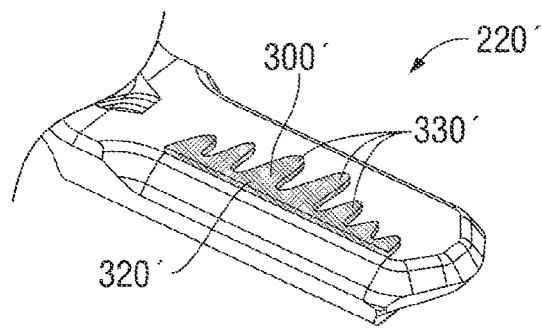
FIG. 5B is an enlarged, side, perspective view of another embodiment of a jaw member configured for use with the end effector assembly of FIG. 3.
Figure 5C:
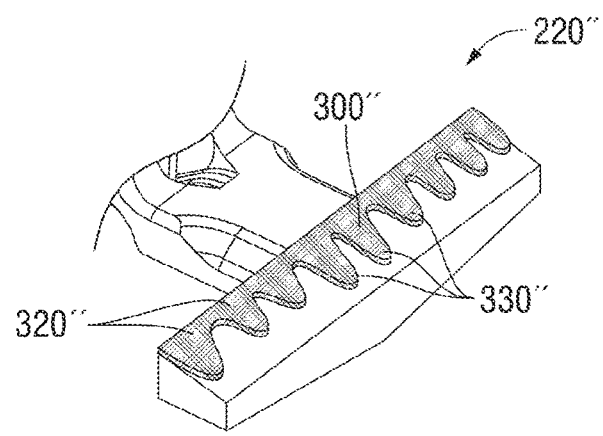
FIG. 5C is an enlarged, side, perspective view of still another embodiment of a jaw member configured for use with the end effector assembly of FIG. 3.

Turning to FIGS. 5B and 5C, various other configurations of jaw members similar to jaw member 220 (FIGS. 3-5A) are shown, although any other suitable configuration may be provided. In particular, FIG. 5B shows a jaw member 220' and FIG. 5C shows a jaw member 220". Jaw member 220' is similar to jaw member 220 (FIGS. 3-5A) except that tissue sealing plate 300' is rotated 90 degrees relative to tissue sealing plate 300 of jaw member 220 (see FIGS. 3-5A) and defines an increased width that extends substantially along the length of jaw member 220'. Tissue sealing plate 300' is raised relative to tissue-grasping surface 224' and includes a main seal portion 320' disposed toward one lateral side of jaw member 220' and an auxiliary seal portion 330' extending from main seal portion 320' towards the other lateral side of jaw member 220'. Tissue sealing plate 300' may otherwise be configured similarly to, or may include any of the features of tissue sealing plate 300 (FIGS. 3-5A), discussed above.

Jaw member 220", as shown in FIG. 5C, is similar to jaw member 220 (FIGS. 3-5A) except that tissue sealing plate 300" is rotated 180 degrees relative to tissue sealing plate 300 of jaw member 220 (see FIGS. 3-5A) and jaw member 220" defines an increased width, or T-shaped configuration. That is, main seal portion 320" is disposed proximally of auxiliary seal portion 330", which extends distally from main seal portion 320" towards the distal end of jaw member 220". Further, the increased width of jaw member 220" is configured to receive a tissue sealing plate 300" having an increased width thereon. Tissue sealing plate 300' may otherwise be configured similarly to, or may include any of the features of tissue sealing plate 300 (FIGS. 3-5A), discussed above. As can be appreciated, different configurations of jaw members, e.g., jaw members 220, 220' and 220", may be suitable for use in different procedures, depending on, for example, the size or configuration of tissue to be sealed and/or other anatomical considerations.

Figure 6:
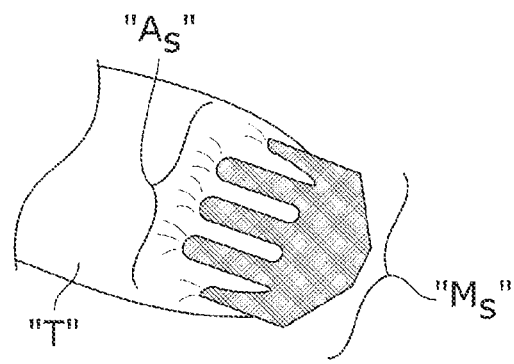
FIG. 6 is a front, perspective illustration of a portion of tissue sealed using the end effector assembly of FIG. 3.

Referring now to FIG. 6, in conjunction with FIGS. 3-5A, the use and operation of end effector assembly 200 will be described. Initially, end effector assembly 200 is manipulated into position such that tissue "T" to be grasped and sealed is disposed between jaw members 210, 220. Next, jaw members 210, 220 are moved from the spaced-apart position to the approximated position to grasp tissue "T" therebetween, e.g., via depressing movable handle 40 relative to fixed handle 50 (see FIG. 1). More particularly, jaw members 210, 220 are moved to the approximated position such that at least a portion of tissue "T" is grasped between tissue sealing plate 300 of jaw member 220 and the tissue sealing plate (not explicitly shown) of jaw member 210. Thereafter, electrosurgical energy may be supplied to tissue sealing plate 300 of jaw member 220 (and/or the tissue sealing plate (not explicitly shown) of jaw member 210), e.g., via activation of actuator 90 (see FIG. 1)) and conducted through tissue to seal tissue "T." Alternatively, actuator 90 may include first and second switches 90a, 90b, respectively, that are selectively and independently activatable to control the supply of energy to main seal portion 320 and auxiliary seal portion 330, respectively (see FIG. 1).

As shown in FIG. 6, the resulting tissue seal includes a generally-arcuate shaped main tissue seal "$M_S$," formed by the main seal portion 320 of tissue sealing plate 300 (FIGS. 3-5), and an auxiliary tissue seal "$A_S$," formed by the auxiliary seal portion 330, e.g., fingers 335, of tissue sealing plate 300 (FIGS. 3-5A), that extends proximally from the main tissue seal "$M_S$." The main tissue seal "$M_S$" ensures that an effective tissue seal has been created, e.g., to seal the luminal (bowel) tissue, and also helps reduce stress concentrations at the seal due to the arcuate-shaped configuration of the main tissue seal "$M_S$," which helps evenly-distribute stresses across the seal. The auxiliary tissue seal "$A_S$" helps further reduce stress concentrations at the main tissue seal "$M_S$" by spreading out the stresses along the auxiliary tissue seal "$A_S$." As can be appreciated, the spaced-apart fingers 335 of auxiliary tissue seal portion 330 of tissue sealing plate 300 create an auxiliary tissue seal "$A_S$" with relatively a large seal perimeter that relieves stress concentrations across the tissue.

The above-described main and auxiliary tissue seals "$M_S$" and "$A_S$," respectively, provide a seal configuration that is particularly advantageous with respect to luminal tissue sealing, e.g., sealing of the bowel, wherein the main tissue seal "$M_S$" may be subject to increased pressures, e.g., during distention of the bowel and/or peristaltic reactions within the bowel. The reduction of stress concentrations, especially during these increased-pressure events, helps ensure that an effective tissue seal is created and maintained and increases the overall burst pressure of the seal.

Turning now to FIGS. 7-9A, another embodiment of an end effector assembly, end effector assembly 400, configured for use with forceps 10 (FIG. 1), forceps 10' (FIG. 2), or any other suitable surgical instrument (not shown) is provided. As shown, end effector assembly 400 is disposed at distal end 14 of shaft 12 of forceps 10 (FIG. 1). Similar to end effector assembly 200, end effector assembly 400 includes first and second jaw members 410, 420, respectively, pivotably coupled to one another about pivot 403 and movable between a spaced-apart position and an approximated position for grasping tissue therebetween. End effector assembly 400 may define a unilateral configuration, as shown, or may alternatively define a bilateral configuration.

With continued reference to FIGS. 7-9A, each jaw member 410, 420 of end effector assembly 400 includes an outer jaw housing 412, 422 and an opposed, tissue-grasping surface 414, 424, respectively. Tissue-grasping surfaces 414, 424 of jaw members 410, 420, respectively, are formed at least partially from an electrically-insulative material. An electrically-conductive tissue sealing plate 500 is disposed at a respective distal end 416, 426 of each tissue-grasping surface 414, 424 such that tissue sealing plates 500 oppose one another. The tissue sealing plates 500 of jaw members 410, 420 are substantially similar and, thus, the tissue sealing plate of jaw member 410 is not shown or described herein to avoid unnecessary repetition.

Figure 7:
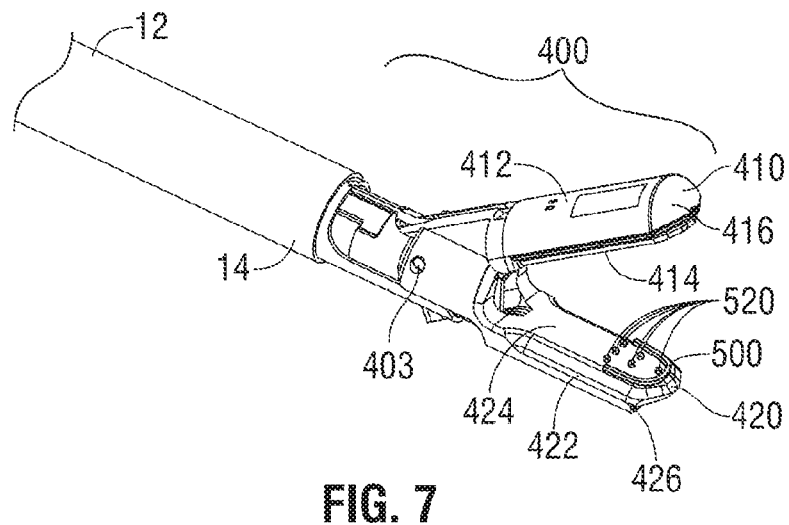
FIG. 7 is a front, perspective view of another embodiment of an end effector assembly configured for use with the surgical instrument of FIG. 1.
Figure 8:
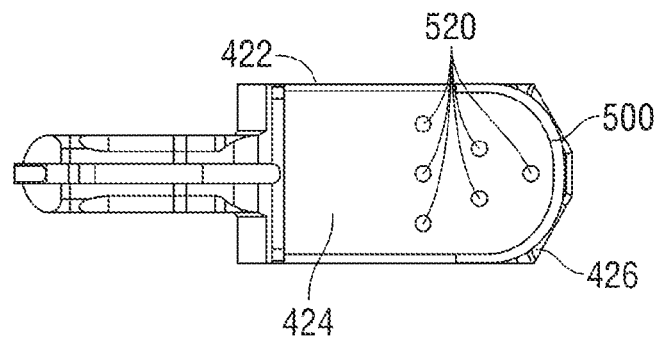
FIG. 8 is top view of one of the jaw members of the end effector assembly of FIG. 7.
Figure 9C:
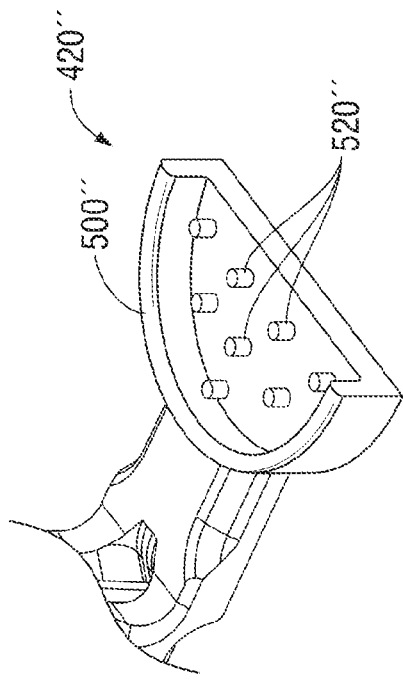
FIG. 9C is an enlarged, side, perspective view of still another embodiment of a jaw member configured for use with end effector assembly of FIG. 7.
Figure 9A:
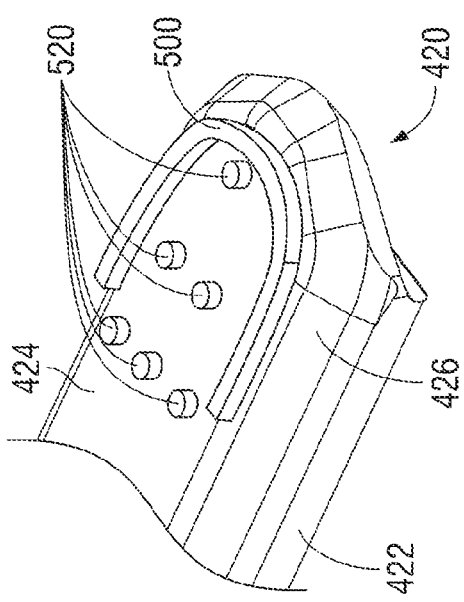
FIG. 9A is a greatly enlarged, side, perspective view of a distal end of the jaw member of FIG. 8.

With continued reference to FIGS. 7-9A, and as best shown in FIGS. 8-9A, tissue sealing plate 500 is disposed at distal end 426 of jaw member 420 and defines a generally U-shaped, or arcuate-shaped configuration. More specifically, tissue sealing plate 500 may be raised relative to tissue-grasping surface 424 of jaw member 420, or may be co-planar with tissue-grasping surface 424. In either configuration, tissue sealing plate 500 is positioned such that, when tissue is grasped between jaw members 410, 420, at least a portion of tissue is disposed between tissue sealing plate 500 of jaw member 420 and the tissue sealing plate (not explicitly shown) of jaw member 410. Tissue sealing plate 500 of jaw member 420, similar to tissue sealing plate 300 of jaw member 220, described above, may also include a flange (not shown), or other suitable feature, that extends into jaw housing 422 to couple tissue sealing plate 500 to a source of electrosurgical energy.

Tissue-grasping surface 424 of jaw member 420 further includes one or more electrically-conductive thermal damage elements 520 disposed thereon and generally-positioned proximally of tissue sealing plate 500. As best shown in FIG. 7, thermal damage elements 520 are disposed generally toward distal end 426 of jaw member 420 and extend from tissue-grasping surface 424, although thermal damage elements 520 may alternatively be co-planar with tissue-grasping surface 424 of jaw member 420. Tissue-grasping surface 414 of jaw member 410 may additionally or alternatively include thermal damage elements (not shown) disposed thereon. Thermal damage elements 520 are spaced-apart from one another and are adapted to connect to a source of electrosurgical energy either independently of, or in conjunction with, tissue sealing plate 500 to supply energy to tissue grasped between jaw members 410, 420 to thermally damage, e.g., damage with RF energy, at least a portion of tissue grasped therebetween. Although six (6) thermal damage elements 520 are shown in triangular-alignment, the configuration and/or quantity of thermal damage elements 520 may be varied. Further, as best shown in FIG. 8, at least one of thermal damage elements 520 may be positioned within the arc-area defined by the arcuate-shaped tissue sealing plate 500.

Figure 9B:
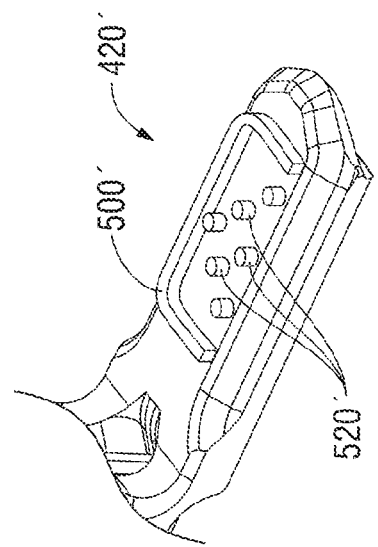
FIG. 9B is an enlarged, side, perspective view of another embodiment of a jaw member configured for use with end effector assembly of FIG. 7.

Turning to FIGS. 9B and 9C, various other configurations of jaw members similar to jaw member 420 (FIGS. 7-9A)

are shown, although any other suitable configuration may be provided. In particular, FIG. 9B shows a jaw member 420' and FIG. 9C shows a jaw member 420". Jaw members 420', 420" each include a generally arcuate-shaped tissue sealing plate 500', 500", respectively, and a plurality of thermal damage elements 520', 520", respectively, disposed adjacent the respective tissue sealing plate 500', 500". Jaw member 420' may include any of the features of jaw member 420 (FIGS. 7-9A), discussed above, and is similar to jaw member 420 (FIGS. 7-9A), except that tissue sealing plate 500' and thermal damage elements 520' are rotated 90 degrees relative to tissue sealing plate 500 and thermal damage elements 520 of jaw member 420 (see FIGS. 7-9A). Jaw member 420" may likewise include any of the features of jaw member 420 (FIGS. 7-9A) and is similar to jaw member 420 (FIGS. 7-9A), except that tissue sealing plate 500" and thermal damage elements 520" are rotated 180 degrees relative to tissue sealing plate 500 and thermal damage elements 520 of jaw member 420 (see FIGS. 7-9A). As can be appreciated, different configurations of jaw members, e.g., jaw members 420, 420' and 420", may be suitable for use in different procedures, depending on, for example, the size or configuration of tissue to be sealed and/or other anatomical considerations.

Figure 10:
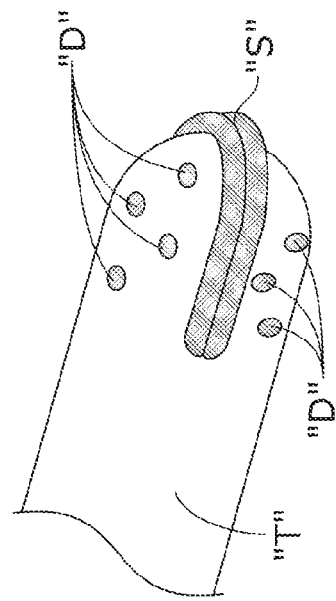
FIG. 10 is a front, perspective illustration of a portion of tissue sealed using the end effector assembly of FIG. 7.

Referring now to FIG. 10, in conjunction with FIGS. 7-9A, the use and operation of end effector assembly 400 will be described. Initially, end effector assembly 400 is manipulated into position such that tissue "T" to be grasped and sealed is disposed between jaw members 410, 420. Next, jaw members 410, 420 are moved from the spaced-apart position to the approximated position to grasp tissue "T" therebetween such that at least a portion of tissue "T" is grasped between tissue sealing plate 500 of jaw member 420 and the tissue sealing plate (not explicitly shown) of jaw member 410. Thereafter, electrosurgical energy may be supplied to tissue sealing plate 500 of jaw member 420 (and/or the tissue sealing plate (not explicitly shown) of jaw member 410), e.g., via activation of actuator 90 (FIG. 1), and conducted through tissue to create a tissue seal "S." The activation of actuator 90 (FIG. 1) may also supply electrical energy to thermal damage elements 520, or thermal damage elements 520 may independently be activated, e.g., actuator 90 may include first and second switches 90a, 90b, respectively, that are selectively and independently activatable to control the supply of energy to tissue sealing plate 500 and thermal damage elements 520, respectively (see FIG. 1). In either configuration, thermal damage elements 520 supply energy to tissue adjacent the tissue seal "S" to thermally-damage tissue adjacent the tissue seal "S."

As shown in FIG. 10, the resulting tissue seal "S" effectively seals tissue "T," e.g., bowel tissue "T." More specifically, tissue seal "S" defines a generally-arcuate shaped configuration that evenly distributes stresses across the seal "S," thereby helping to reduce stress concentrations at the seal "S." The thermal damage "D" to tissue adjacent the tissue seal "S" inhibits the peristaltic reaction of the tissue surrounding the tissue seal "S," thereby reducing the stresses imparted to tissue seal "S." The thermal damage "D" to tissue also limits the distention of the tissue adjacent the tissue seal "S." Thus, similarly as above, the reduction in stress concentrations at the seal "S," and the reduction of stresses imparted to the seal "S" helps ensure that an effective tissue seal is created and maintained and increases the overall burst pressure of the seal "S." Further, the thermal damage "D" to tissue adjacent the tissue seal "S," which inhibits peristaltic reactions and limits distention, allows the tissue seal "S" to sufficiently form, e.g., the thermal damage "D" protects the tissue seal "S" from increased stresses as the tissue seal "S" is in the initial formation and strengthening stages (i.e., as the tissue heals).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   an end effector assembly including first and second jaw members, at least one of the first or second jaw members moveable relative to the other of the first or second jaw members between a spaced-apart position and an approximated position to grasp tissue therebetween, at least one of the first or second jaw members including:
   an electrically-insulative tissue-grasping surface defining a peripheral edge;
   an electrically-conductive tissue sealing plate defining a continuously flat upper surface, the electrically-conductive tissue sealing plate disposed on the peripheral edge of the electrically-insulative tissue-grasping surface, the electrically-conductive tissue sealing plate having a U-shaped configuration and defining an interior area, the electrically-conductive tissue sealing plate configured to conduct energy through the tissue grasped between the first and second jaw members to create a tissue seal, the electrically-conductive tissue sealing plate raised with respect to the electrically-insulative tissue-grasping surface away from the first or second jaw members; and
   a plurality of discrete thermal damage elements disposed on the electrically-insulative tissue-grasping surface and positioned within the interior area, the plurality of thermal damage elements configured to conduct energy through the tissue to thermally-damage the tissue adjacent the tissue seal.

2. The forceps according to claim 1, wherein the U-shaped configuration of the electrically-conductive tissue sealing plate includes an arcuate portion.

3. The forceps according to claim 1, wherein the electrically-insulative tissue-grasping surface defines a first plane and wherein the electrically-conductive tissue sealing plate defines a second plane disposed in parallel orientation relative to the first plane.

4. The forceps according to claim 3, wherein the plurality of discrete thermal damage elements define a third plane disposed in parallel orientation relative to the first plane.

5. The forceps according to claim 4, wherein the second and third planes are co-planar.

6. The forceps according to claim 1, wherein the electrically-conductive tissue sealing plate is oriented such that the interior area faces a proximal end portion of the at least one of the first or second jaw members.

7. The forceps according to claim 1, wherein each of the plurality of thermal damage elements is surrounded by the electrically-insulative tissue-grasping surface.

8. The forceps according to claim 1, wherein at least one of the plurality of thermal damage elements defines a circular configuration.

9. The forceps according to claim 1, further comprising first and second switches, the first and second switches selectively and independently activatable for controlling the supply of energy to the electrically-conductive tissue sealing plate and the plurality of thermal damage elements, respectively.

10. The forceps according to claim 1, further comprising at least one additional discrete thermal damage element disposed on the electrically-insulative tissue-grasping surface and positioned outside the interior area, the at least one additional thermal damage element configured to conduct energy through tissue to thermally-damage tissue.

11. An end effector assembly of a forceps, comprising:
   first and second jaw members, at least one of the first or second jaw members moveable relative to the other of the first or second jaw members between a spaced-apart position and an approximated position to grasp tissue therebetween, each of the first and second jaw members including:
      an electrically-insulative tissue-grasping surface defining a peripheral edge; and
      an electrically-conductive tissue sealing plate defining a continuously flat upper surface, the electrically-conductive tissue sealing plate disposed on the peripheral edge of the electrically-insulative tissue-grasping surface, the electrically-conductive tissue sealing plate having a U-shaped configuration and defining an interior area, the electrically-conductive tissue sealing plates configured to conduct energy through the tissue disposed therebetween to create a tissue seal, the electrically-conductive tissue sealing plate raised with respect to the electrically-insulative tissue-grasping surface away from the first or second jaw members,
   at least one of the first or second jaw members including:
      a plurality of discrete thermal damage elements disposed on the electrically-insulative tissue-grasping surface thereof and positioned within the interior area, the plurality of thermal damage elements configured to conduct energy through the tissue to thermally-damage the tissue adjacent the tissue seal.

12. The end effector assembly according to claim 11, wherein the electrically-conductive tissue sealing plates are oriented such that the interior areas thereof face proximal end portions of the respective first and second jaw members.

13. The end effector assembly according to claim 11, wherein the at least one of the first or second jaw members further includes at least one additional discrete thermal damage element disposed on the electrically-insulative tissue-grasping surface thereof and positioned outside the interior area, the at least one additional thermal damage element configured to conduct energy through tissue to thermally-damage tissue.

14. The end effector assembly according to claim 11, wherein the U-shaped configurations of the electrically-conductive tissue sealing plates each include an arcuate portion.

* * * * *